(12) United States Patent
Maughan et al.

(10) Patent No.: US 8,099,304 B2
(45) Date of Patent: *Jan. 17, 2012

(54) SYSTEM AND USER INTERFACE FOR PROCESSING PATIENT MEDICAL DATA

(75) Inventors: Rex Wendell Maughan, Murray, UT (US); Jeffrey D. Lee, Grantsville, UT (US); Jennel L. McCoy, Salt Lake City, UT (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1080 days.

This patent is subject to a terminal disclaimer.

(21) Appl. No.: 11/456,688

(22) Filed: Jul. 11, 2006

(65) Prior Publication Data

US 2007/0055545 A1    Mar. 8, 2007

Related U.S. Application Data

(60) Provisional application No. 60/713,807, filed on Sep. 2, 2005.

(51) Int. Cl.
*A61B 5/00* (2006.01)
*G06F 19/00* (2011.01)

(52) U.S. Cl. ......................................................... 705/3

(58) Field of Classification Search .................... 705/2, 3
See application file for complete search history.

(56) References Cited

U.S. PATENT DOCUMENTS

| | | | | |
|---|---|---|---|---|
| 5,255,187 A | * | 10/1993 | Sorensen | 600/300 |
| 5,544,661 A | * | 8/1996 | Davis et al. | 600/513 |
| 5,576,952 A | * | 11/1996 | Stutman et al. | 600/300 |
| 5,942,986 A | * | 8/1999 | Shabot et al. | 340/7.29 |
| 6,278,999 B1 | * | 8/2001 | Knapp | 707/9 |
| 6,383,136 B1 | * | 5/2002 | Jordan | 600/300 |
| 6,789,019 B2 | | 9/2004 | Hirai | |

(Continued)

FOREIGN PATENT DOCUMENTS

WO    0166000 A2    9/2001

OTHER PUBLICATIONS

PhysioBank Archive Index http://www.physionet.org/physiobank/database.

(Continued)

*Primary Examiner* — Gerald J. O'Connor
*Assistant Examiner* — Trang Nguyen
(74) *Attorney, Agent, or Firm* — Alexander J Burke

(57) ABSTRACT

A clinical data processing system systematically organizes and analyzes clinically significant information of a patient using a result flag indicating a critical or abnormal result to automate display of a view of clinical data in various contexts including diagnosis, insurance, medical complaint assessment and others to improve patient care. A system for use in processing patient clinical data for access by a user includes a repository associating an observation with a clinical significance indicator and with data indicating observations relevant to evaluation of the observation having the associated clinical significance indicator. A clinical data processor uses the repository fork automatically providing data for display in response to receiving data representing an input observation and an associated clinical significance indicator. The data for display supports a user in making a patient assessment and includes the input observation and associated relevant clinical data items. A display processor initiates generation of data representing an image including the data for display.

23 Claims, 10 Drawing Sheets

U.S. PATENT DOCUMENTS

| | | | |
|---|---|---|---|
| 6,804,656 B1 * | 10/2004 | Rosenfeld et al. | 705/3 |
| 6,810,282 B2 * | 10/2004 | Taha et al. | 600/509 |
| 7,147,600 B2 * | 12/2006 | Bardy | 600/300 |
| 2001/0050610 A1 * | 12/2001 | Gelston | 340/5.53 |
| 2003/0065535 A1 | 4/2003 | Karlov | |
| 2003/0074248 A1 * | 4/2003 | Braud et al. | 705/9 |
| 2004/0078231 A1 * | 4/2004 | Wilkes et al. | 705/2 |
| 2005/0209882 A1 * | 9/2005 | Jacobsen et al. | 705/2 |
| 2006/0135859 A1 | 6/2006 | Iliff | |

OTHER PUBLICATIONS

Goldberger A. L. et al., Components of a New Research Resource for Complex Physiologic Signals, Physiobank, Physiotoolkit, and Physionet, http://www.circulationaha.org.

* cited by examiner

| Rules Type | Rule Information | Actions | External Result | Comments |
|---|---|---|---|---|
| Result Type | If type = Normal | Add 1 to n specific results as defined for this result value and/or add 1 to n collections of results/observations (flowsheets) | Add Values to Result Set | |
| | If type = Abnormal | Add 1 to n specific results as defined for this result value and/or add 1 to n collections of results/observations (flowsheets) | Add Values to Result Set | |
| | If type = Critical | Add 1 to n specific results as defined for this result value and/or add 1 to n collections of results/observations (flowsheets) | Add Values to Result Set | |
| Working Diagnosis | Check for specific result - Include | If specific result is present and has a specific critical/abnormal flag | Add Values to Result Set | |
| | Check for specific result - Exclude | If specific result is present and does not have the specific critical/abnormal flag | Exclude Values from Result Set | |
| Problem List | If specific problem is present | Add 1 to n specific results as defined for this result value and/or add 1 to n collections of results/observations (flowsheets) | Add Values to Result Set | |
| | If specific problem is absent | Add 1 to n specific results as defined for this result value and/or add 1 to n collections of results/observations (flowsheets) | Add Values to Result Set | |
| Family History | If specific family history indicator is absent | Add 1 to n specific results as defined for this result value and/or add 1 to n collections of results/observations (flowsheets) | Add Values to Result Set | |
| | If specific family history indicator is present | Add 1 to n specific results as defined for this result value and/or add 1 to n collections of results/observations (flowsheets) | Add Values to Result Set | |
| Patient History | If specific patient history indicator is absent | Add 1 to n specific results as defined for this result value and/or add 1 to n collections of results/observations (flowsheets) | Add Values to Result Set | |
| | If specific patient history indicator is present | Add 1 to n specific results as defined for this result value and/or add 1 to n collections of results/observations (flowsheets) | Add Values to Result Set | |
| Medications | Include specific medications | Select results related to the specific medication | Add Values to Result Set | |
| | Exclude specific medications | Exclude results related to the specific medication | Exclude value(s) from Result Set | |
| Other Results and/or Observations | Include specific results | Select results related regardless of their critical/abnormal flag | Add Values to Result Set | |
| | Exclude specific medications | Exclude results related regardless of their critical/abnormal flag | Exclude value(s) from Result Set | |
| Allergies | Include specific allergy (or allergies) | Select the specific allergy if present | Add Values to Result Set | A specific allergy may be important to a specific result |
| Insurance | Include specific insurance details | Include specific insurance details based on triggering result | Add Insurance information to Result Set | Can be used to validate if patient can use a specific service like Physical |

FIGURE 6

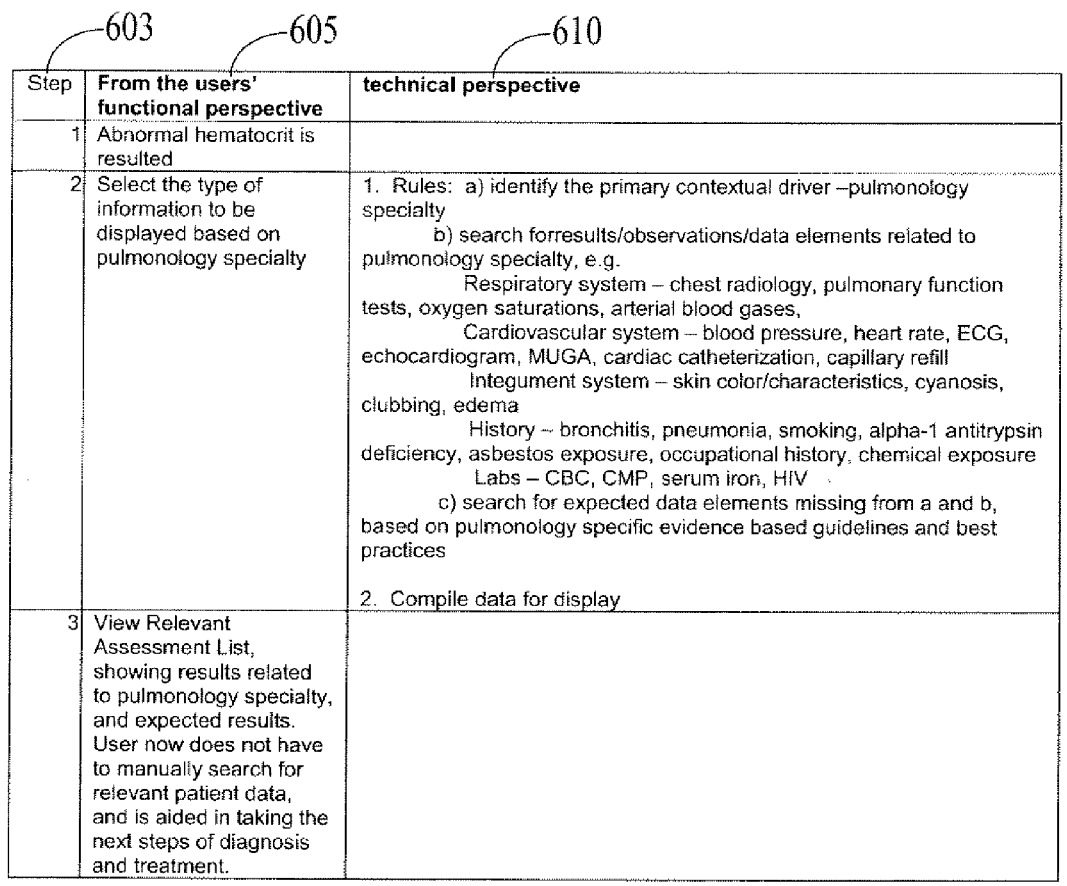

| Step | From the users' functional perspective | technical perspective |
|---|---|---|
| 1 | Abnormal hematocrit is resulted | |
| 2 | Select the type of information to be displayed based on pulmonology specialty | 1. Rules:  a) identify the primary contextual driver –pulmonology specialty<br>b) search forresults/observations/data elements related to pulmonology specialty, e.g.<br>    Respiratory system – chest radiology, pulmonary function tests, oxygen saturations, arterial blood gases,<br>    Cardiovascular system – blood pressure, heart rate, ECG, echocardiogram, MUGA, cardiac catheterization, capillary refill<br>    Integument system – skin color/characteristics, cyanosis, clubbing, edema<br>    History – bronchitis, pneumonia, smoking, alpha-1 antitrypsin deficiency, asbestos exposure, occupational history, chemical exposure<br>    Labs – CBC, CMP, serum iron, HIV<br>c) search for expected data elements missing from a and b, based on pulmonology specific evidence based guidelines and best practices<br><br>2. Compile data for display |
| 3 | View Relevant Assessment List, showing results related to pulmonology specialty, and expected results. User now does not have to manually search for relevant patient data, and is aided in taking the next steps of diagnosis and treatment. | |

FIGURE 7

| Step | From the users' functional perspective | From the programmers' technical perspective |
|---|---|---|
| 1 | Select the type of information to be displayed based on cancer as a working diagnosis | 1. Rules: a) identify the secondary contextual driver – cancer<br>b) search for results/observations/data elements related to cancer, e.g.<br>    Respiratory system – abnormal chest radiography, bronchoscopy, biopsy<br>    Cardiovascular system – DVT, abnormal coagulation<br>    Integument system – moles, warts, lumps, sun exposure<br>    History – weight loss, family members with cancer, down winder, previous biopsies, fractures, radiation exposure<br>    Labs – bone marrow, coags, CEA, calcium, peripheral smear,<br>c) search for expected data elements missing from a and b, based on cancer specific evidence based guidelines and best practices<br><br>2. Compile data for display |
| 2 | View Relevant Assessment List, showing results related to oncology specialty and evidence of signs/risks of cancer, and expected results. | |

FIGURE 8

| Step | From the users' functional perspective | From the programmers' technical perspective |
|---|---|---|
| 1 | Abnormal hematocrit is resulted | |
| 2 | Select the type of information to be displayed based on endocrinology specialty | 1. Rules: a) identify the primary contextual driver – endocrinology specialty<br>b) search for results/observations/data elements related to endocrinology specialty, e.g.<br>    Respiratory system – chest radiology, pulmonary function tests, oxygen saturations, arterial blood gases,<br>    Cardiovascular system – blood pressure, heart rate, ECG, echocardiogram, MUGA, cardiac catheterization, capillary refill<br>    Integument system – skin color/characteristics, cyanosis, clubbing, edema<br>    History – bronchitis, pneumonia, smoking, alpha-1 antitrypsin deficiency, asbestos exposure, occupational history, chemical exposure<br>    Labs – CBC, CMP, serum iron, HIV<br>c) search for expected data elements missing from a and b, based on endocrinology specific evidence based guidelines and best practices<br><br>2. Compile data for display |
| 3 | View Relevant Assessment List, showing results related to endocrinology specialty, and expected results. User now does not have to manually search for relevant patient data, and is aided in taking the next steps of diagnosis and treatment. | |

FIGURE 9

| Step | From the users' functional perspective | From the programmers' technical perspective |
|---|---|---|
| 1 | Select the type of information to be displayed based on expected results and observations. | 1. Rules: a) identify the tertiary contextual driver – expected results and observations<br>    b) search for results/observations/data elements related to expected results/observations/data, e.g.<br>        Respiratory system – presence of a tumor on radiography, presence of malignant cells on bronchoscopy or biopsy<br>        Cardiovascular system – DVT, abnormal coagulation<br>        Integument system – moles, warts, lumps, sun exposure<br>        History – weight loss, family members with cancer, down winder, previous biopsies, fractures, radiation exposure<br>        Labs – bone marrow, coags, CEA, PSA, BRCA-1, calcium, peripheral smear,<br>    c) search for expected data elements missing from a and b, based on cancer specific evidence based guidelines and best practices<br><br>2. Compile data for display |
| 2 | View Relevant Assessment List, showing results related to oncology specialty and evidence of signs/risks of cancer, and expected results. | |

SYSTEM AND USER INTERFACE FOR PROCESSING PATIENT MEDICAL DATA

This is a non-provisional application of provisional application Ser. No. 60/713,807 by R. Maughan et al. filed Sep. 2, 2005.

FIELD OF THE INVENTION

This invention concerns a system for providing data indicating clinical significance of a received clinical data item and for providing information relevant to evaluation of a received clinical data item and supporting making a patient assessment.

BACKGROUND OF THE INVENTION

In hospitals and other patient treatment facilities clinicians are typically inundated with vast amounts of patient medical data. Exisitng systems allow users to view clinical information as individual items or, in context based on entry of data indicating a preferred viewing configuration or in response to data indicating a predetermined preferred viewing configuration. Thereby existing systems typically allow a user to view information in a rudimentary way, e.g., as individual information items or as a small group of information items. Existing systems also require a clinician to remember associated results that should be reviewed and to search and select each of the associated results and to view these results. Consequently, existing systems are vulnerable to a healthcare worker failing to perform a review of results and may experience an additional time delay involved in recovery from such a failure and other human errors. A system according to invention principles addresses these deficiencies and related problems.

SUMMARY OF THE INVENTION

A clinical data processing system systematically organizes and analyzes clinically significant information of a patient using a result flag indicating a critical or abnormal result, for example, to infer data associations and customize displayed data to include specific abnormal or critical results and calculate associated expected results or other results of interest. A system for use in processing patient clinical data for access by a user includes, a repository associating, an observation with a clinical significance indicator and with data indicating observations relevant to evaluation of the observation having the associated clinical significance indicator. A clinical data processor uses the repository for automatically providing data for display in response to receiving data representing an input observation and an associated clinical significance indicator. The data for display supports a user in making a patient assessment and includes the input observation and associated relevant clinical data items. A display processor initiates generation of data representing an image including the data for display.

BRIEF DESCRIPTION OF THE DRAWINGS

FIG. 4 shows a specialized patient observations display provided in response to observation selection from the assessment list of FIG. 3, according to invention principles.

FIG. 5 shows different types of rules employed by a clinical data processing system in providing a customized contextual patient results display, according to invention principles.

FIG. 6 shows steps and rules involved in providing clinically significant data concerning a medical specialty condition, according to invention principles.

FIG. 7 shows steps and rules involved in providing clinically significant data supporting oncology diagnosis, according to invention principles.

FIG. 8 shows steps and rules involved in providing clinically significant data supporting an endocrinology specialty, according to invention principles.

FIG. 9 shows steps and rules involved in providing clinically significant data concerning an oncology condition, according to invention principles.

DETAILED DESCRIPTION OF THE INVENTION

A system according to invention principles organizes and analyzes clinically significant information including pertinent patient data. The system provides a systematic method of organizing and analyzing pertinent patient data for customized display by using a results indicator and a result critical or abnormal flag as well as predetermined rules in inferring data associations. The system allows clinicians to select specific abnormal or critical results and calculate associated expected results or other results of interest. The system improves patient care by using automation to help a clinician view patient medical data in various contexts including for diagnosis, for insurance purposes, complaint assessment and many other contexts. The system involves selection of a single patient medical observation and use of a processor for applying predetermined rules to determine inferences that are made based upon a type of the observation and associated information appropriate for the context of the observation. An observation comprises a patient medical parameter including at least one of, (a) a blood pressure parameter, (b) a ventilation parameter, (c) a vital sign parameter, (d) a blood oxygen concentration representative parameter, (e) a spontaneous tidal volume parameter, (t) a respiratory rate parameter, (g) a positive end-expiratory pressure parameter, (h) a temperature, (i) a heart rate, (j) a cardiac output, (k) an infusion pump parameter associated with fluid delivery, (l) a drip medication related parameter, (m) another fluid related parameter, (n) a parameter in a patient medical record (p) a laboratory test result, and (q) a calculated score, such as from the Braden Scale, a pain scale, an intake and/or output summary, or nutrition risk assessment. The contextual association, along with the rules, support creation of data determining both the data displayed and the display format used.

Figure 1:
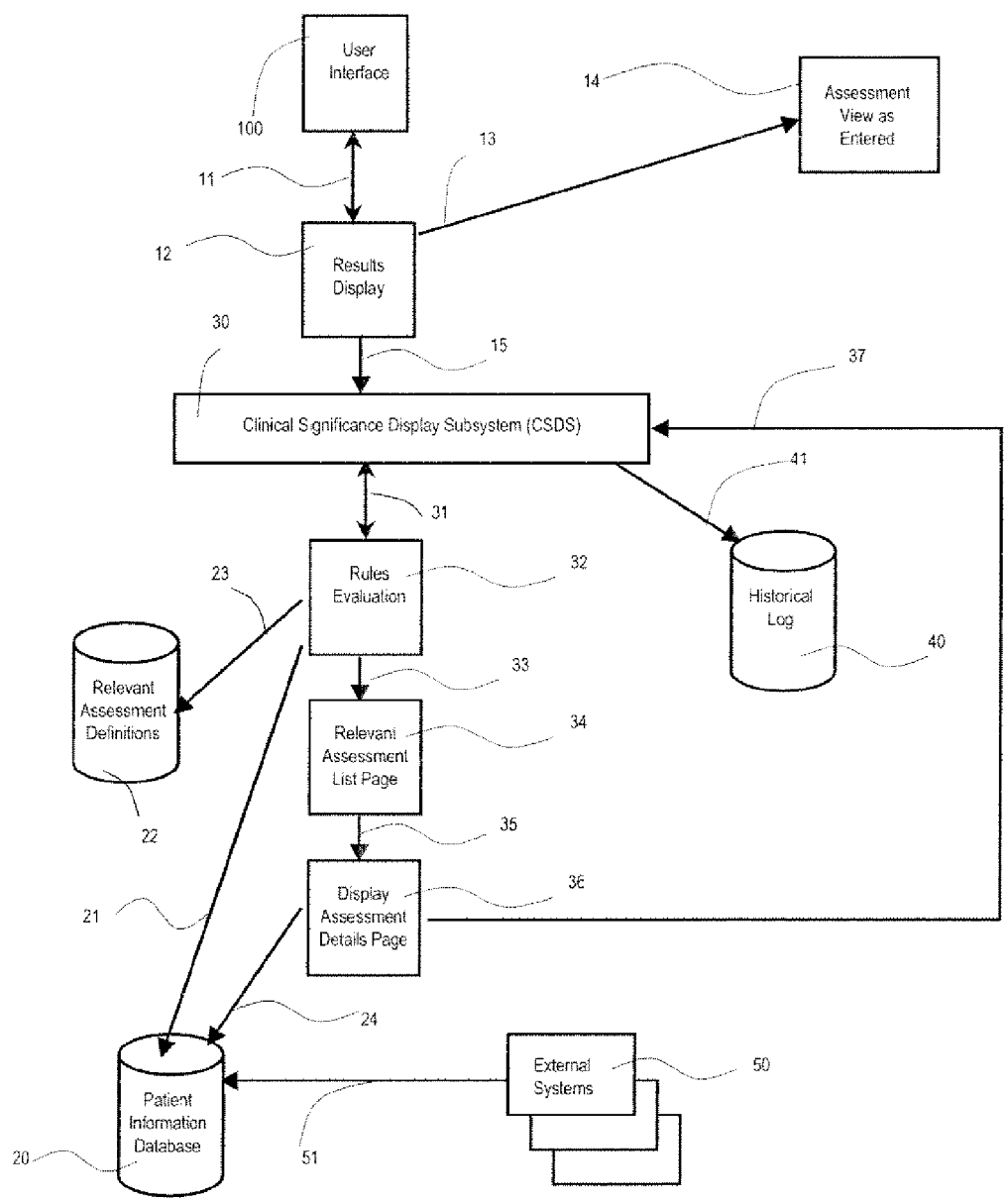
FIG. 1 shows a clinical data processing system, according to invention principles.

FIG. 1 shows a clinical data processing system 10 for organizing data in an image display by mutually associating contextual observations already in the system according to predetermined rules as well as indicators such as normal, abnormal, or critical result indicators, and parameter identifying a diagnosis, a differential diagnosis, a medical specialty, a principal complaint, insurance coverage, allergies, past medical history, family history, social history, medications, and a problem list. System 10 identifies what is expected as a result of an observation. This is done based on the observation as well as on data subsequently acquired that is advantageously analyzed together with the observation. System 10 identifies to a user the subsequently acquired data to be analyzed together with the observation via a displayed image.

System 10 initiates rules for organizing data in an image display. The rules are selected based on a relationship of an observation to an expected result, a result out of context with other results, or a result that is out of context with anything that initiates the rules. System 10 organizes data for display in an image logically, based on the context of an observation and questions associated with the observation. Advantageously clinical data (including observations) is displayed ill context with other physiological parameters associated with the clinical data (e.g. an observation). System 10 facilitates standardized thorough evaluation and analysis as well as diagnoses that are evidence based and system 10 provides a differential diagnosis list that is exhaustive. This promotes better outcomes for patients, and a more timely and accurate diagnosis and treatment. The system manages patient clinical data from a contextual association approach by displaying pertinent patient data associated with a single observation. For example, if a patient has low hemoglobin, rather than just displaying this observation in the context of a CBC (Complete Blood Count) result, any result associated with this observation is displayed, such as oxygen saturation, arterial blood gas, serum iron studies, and blood pressure, for example. System 10 executes predetermined rules enabling an oncologist to include in the display of the hemoglobin observation a bone marrow aspirate, and current chemotherapy treatments, for example.

Context of an observation, as used herein, comprises a type (category) of an observation together with other parameters including physiological parameters and indicators that are advantageously associated with the observation and that support user or automatic processor determination of inferences that facilitate diagnosis of a patient by a physician or support insurance reimbursement or aid complaint assessment or facilitate other tasks.

An executable application as used herein comprises code or machine readable instruction for implementing predetermined functions including those of an operating system, healthcare information system or other information processing system, for example, in response user command or input. An executable procedure is a segment of code (machine readable instruction), sub-routine, or other distinct section of code or portion of an executable application for performing one or more particular processes and may include performing operations on received input parameters (or in response to received input parameters) and provide resulting output parameters. A processor as used herein is a device and/or set of machine-readable instructions for performing tasks. A processor comprises any one or combination of, hardware, firmware, and/or software. A processor acts upon information by manipulating, analyzing, modifying, converting or transmitting information for use by an executable procedure or an information device, and/or by routing the information to an output device. A processor may use or comprise the capabilities of a controller or microprocessor, for example. A display processor or generator is a known element comprising electronic circuitry or software or a combination of both for generating display images or portions thereof. A user interface comprises one or more display images enabling user interaction with a processor or other device.

System 10 mutually associates contextual observations already in the system and enables clinical results and associated abnormal observation indicators to govern display of clinical data of a patient. If an observation is indicated as critical or abnormal, system 10 automatically initiates generation of a predetermined, specialized assessment image view showing other relevant data for display to a user. System 10 generates multiple different predetermined, specialized assessment image views and enables a user to select a particular view for display from the multiple different views. In response to a user selecting multiple views, system 10 automatically combines and merges clinical data associated with each selected view, removing redundant duplicated data, for display in a composite view.

System 10 employs a rules evaluation processor that uses information derived from multiple sources, together with associated critical or abnormal clinical significance indicators, to determine a relevant medical condition assessment list. The multiple sources include, for example, patient medical history, family medical history, diagnosis, specialties, patient complaints, insurance, allergies, medications, a problem list and other results. Other observations are processed by the rules evaluation processor using a template created by system 10 that describes an individual observation. In one embodiment an individual observation is tagged with a clinical significance indicator identifying one of multiple different statuses including, a) abnormal expected, b) normal expected, c) view or d) do not care. In response to the rules evaluation processor 32 in system 10 analyzing an individual patient observation and determining observation indicators do not match expected values, system 10 provides the expected values to a user in a display image visually flagged for easier identification of the discrepancy. System 10 advantageously processes clinical result data for display and is usable by a wide variety of clinical results display applications.

Figure 3:
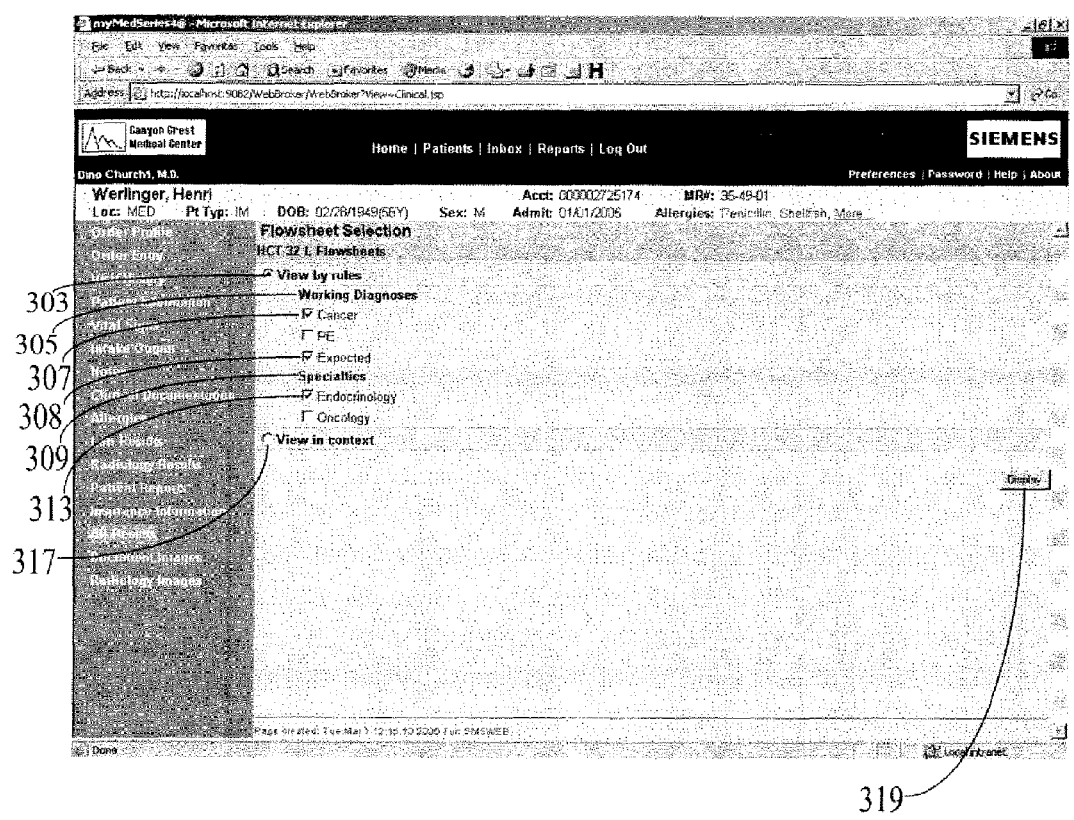
FIG. 3 shows an assessment list page provided by a clinical data processing system enabling a user to select type of information to be displayed based on diagnosis and rules, according, to invention principles.

A user interacts with clinical data processing system 10 of FIG. 1 via User Interface 100 to access data representing a results display image 12 through communication path 11. Results display image 12 shows patient observations associated with a user request for patient information. In particular, results display image 12 presents data representing an entered patient medical assessment 14 accessed via communication path 13 in response to a user command. This allows a user to use existing functions to display patient observations and medical assessments 14. In response to a user choosing to view observations using Clinical Significance Subsystem (CSDS) 30, a user selects a desired option from a user interface menu display image 12. FIG. 3 (described later) gives an example of the relevant assessment list page presented in display image 12 where a user selects the type of information to be displayed based on diagnosis and/or specialty rules. Data indicating the desired options selected via the FIG. 3 menu is communicated to CSDS subsystem 30 through communication interface 15. Data indicating the activities occurring and performed by system 10 are provided by CSDS subsystem 30 to historical log (and audit record) repository 40 through communication interface 41. This information is used for support of governmental regulations, to evaluate rules engine performance or to help improve quality and accuracy of relevant assessment definitions 22 in a database.

Figure 2:
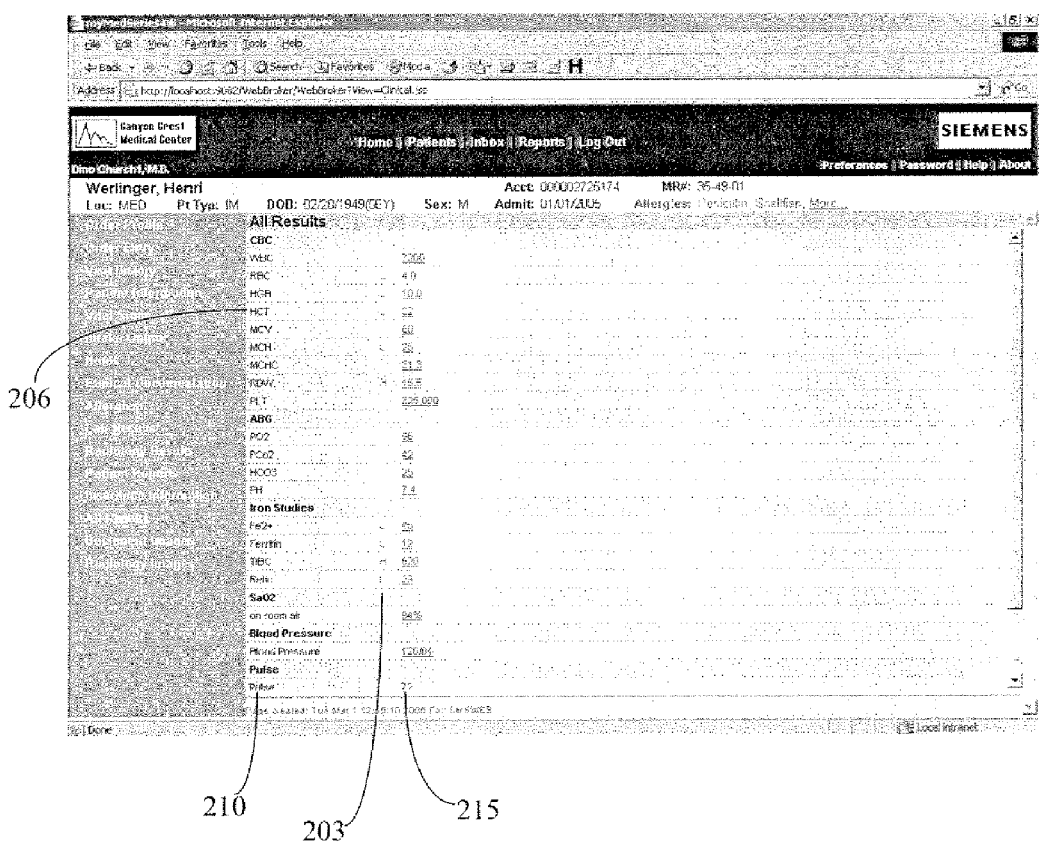
FIG. 2 shows a customized contextual patient results display provided by a clinical data processing system for use by a family care physician, according to invention principles.

Data indicating the desired options selected via the FIG. 3 user interface menu (display image 12) is also communicated via interface 31 to rules evaluation engine 32. Rules evaluation engine 32 acquires specific patient information, such as demographic, clinical and/or financial information by accessing patient information database 20 through communication interface 21. The relevant assessment definitions 22 indicate for an individual observation an associated collection of clinical information (data presented in a medical flowsheet, for example). System 10 displays an observation together with an associated collection of clinical information if an observation indicator indicates the observation is normal, or displays an additional list of information if an observation clinical significance indicator is abnormal and a third different list of information if an observation indicator is critical. In response to the type of indicator (e.g., normal, abnormal, critical) of an observation, system 10 displays either a list of assessments or clinical observations as illustrated in FIG. 2 (described later) or a single assessment or observation. System 10 provides a means for bringing patient data into clinical context, facilitating timeliness, accuracy, and thoroughness of diagnoses and treatment, thus improving patient treatment outcomes.

A physician or other clinician stores in system 10 data comprising a predetermined set of working diagnoses that may be associated with a specific result indicator. For example, a clinician may have indicated that if a Hematocrit result (item 206 of FIG. 2) is abnormal, a working diagnosis of cancer or pulmonary embolus is to be included. In response to user selection of a working diagnosis via interface 100, system 10 selects expected observations associated with the working diagnosis using rules evaluation engine 32 and assessment list page 34. System 10 obtains a list of expected observations for the patient in response to each additional working diagnosis selected by a user. Rules evaluation engine 32 identifies working diagnosis related observations and also identifies and removes duplicate observations and consolidates the resultant observations for display. In addition, if a user selects a displayed Expected indicator associated with working diagnoses, individual observations are analyzed to determine if an expected observation for these working diagnoses should be normal, abnormal or critical. Patient observation clinical significance indicators that do not match the expected abnormal, critical, normal indicators are visually marked to notify a clinician of the discrepancy. The results provided by Rules evaluation engine 32 are summarized in relevant assessment list page 34 through communication interface 33.

FIG. 3 gives an example of relevant assessment list page 34 enabling a user to select the type of information to be displayed based on diagnosis and/or specialty rules. Multiple observation display options are available through application of rules illustrated in the rules table of FIG. 5. Specifically, FIG. 5 shows rules employed by Rules evaluation engine 32 in organizing and collating observations related to a working diagnosis and in identifying and removing duplicate observations in consolidating the resultant observations for display. The FIG. 5 table gives examples of the different types of rules (column 503) that are stored in Relevant Assessment Definition database 22. The stored rules are selectively used in any combination enabling a user to specify clinical information for customized display in a variety of ways to meet the needs of a clinician. The rules direct addition, selection or exclusion of particular observations from a display image as indicated in columns 507 and 513 with a condition based on inputs indicated in column 505. Additional implications and comments are indicated in column 517. In response to execution of the rules upon a patient data request, rules evaluation engine 32 removes duplicates from an observation result set and excludes identified items from the result set. After the exclusion is completed, the result is formatted and displayed in the Display Assessment Details Page 36.

Assessment list page 34 of FIG. 3 provided by clinical data processing system 10 enables a user to select type of information to be displayed based on diagnosis and rules. The assessment list page in this example enables a user to select the type of patient information to be displayed based on predetermined rules via option 303 and/or based on context via option 317. Here a user selects option 303 to provide an image view determined based on predetermined rules for a diagnosis 305 indicating an expected cancer context 307, 308 (selected by a user). A user further refines the patient information to be displayed by selecting a specialty 309, specifically, endocrinology 313. A user initiates display of a view of observations as configured using the FIG. 3 menu via button 319, for example. Specifically, a user selects assessment list items for display and system 10 processes this request to provide results displayed in a display assessment list page 36 via interface 35.

Figure 4:
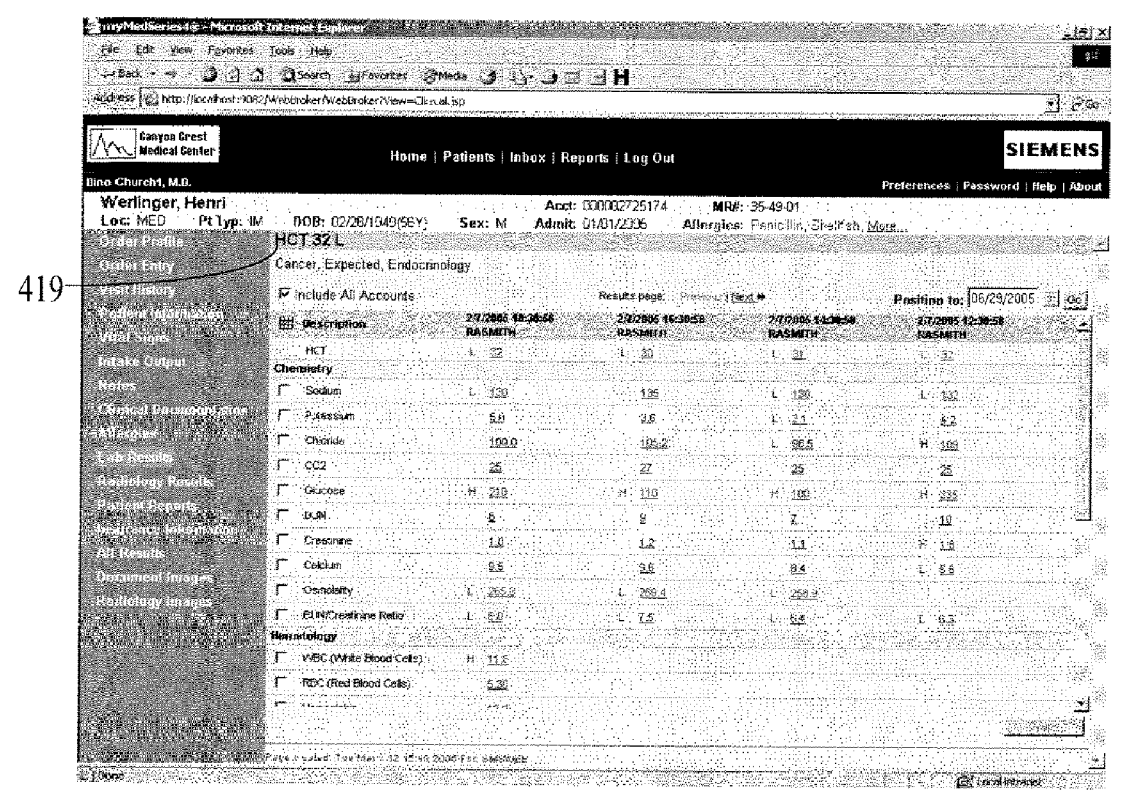

FIG. 2 illustrates a customized contextual patient observation assessment list display 36 provided by system 10 for use by a family care physician. Assessment list display 36 presents patient observation identifier labels in column 210 and corresponding observation values in column 215. Column 203 displays observation clinical significance indicators. Specifically, column 203 includes indicators that are critical identified by L and H letters (L indicates abnormally low values, H abnormally high values). These indicators may be emphasized by visual attributes including color (such as red), highlighting, shading, shape, text and symbols, for example. A patient hematocrit observation (HCT item 206) has an abnormally low value, for example. A user is able to select a specific observation (e.g., HCT item 206) on assessment list display 36 and request a new analysis through CSDS 30 via communication path 37. FIG. 4 shows a specialized patient observations display provided by CSDS 30 and rules evaluation engine 32. Rules engine 32 applies the predetermined steps and rules of FIGS. 6 through 9, for example, in providing clinically significant data concerning a medical specialty condition (e.g., associated with an abnormal HCT value 419) as illustrated in FIG. 4. Specifically, FIG. 4 shows a collection of clinical information associated with an abnormal HCT item derived from assessment definitions 22 by rules evaluation engine 32 working in conjunction with CSDS 30, in response to user selection of HCT item 206 in the assessment list of FIG. 2.

FIGS. 6 through 9 illustrate predetermined steps and rules employed by evaluation engine 32 working in conjunction with CSDS 30 and assessment definitions 22 in organizing clinically significant data for a particular specialty in response to determination of an abnormal HCT. In particular, FIG. 6 shows organizing clinically significant data for a pulmonology specialist in response to determination of an abnormal HCT for a patient having medical data accessible by system 10. Column 603 and corresponding columns 605 and 610 indicate user functional interaction steps and rules applied by units 22, 30 and 32 in organizing patient clinical data for a pulmonology specialist.

In response to detection of a patient abnormal HCT value in step 1 (column 603) and user selection of a pulmonology specialty view in step 2, units 30 and 32 in conjunction initiate a search of assessment definitions 22 and patient data database 20 for observations and data elements related to a pulmonology specialty, including observations and data concerning multiple systems. The multiple system observations include respiratory system observations (chest radiology, pulmonary function tests, oxygen saturation results, arterial blood gas results), cardiovascular system observations (blood pressure, heart rate, ECG, echocardiogram, MUGA, cardiac catheterization, capillary refill), integument system observations (skin color and characteristics, cyanosis, clubbing, edema) and medical history (bronchitis, pneumonia, smoking, alpha-1 antitrypsin deficiency, asbestos exposure, occupational history, chemical exposure, laboratory test results, CBC, CMP, serum iron, HIV). Units 30 and 32 in conjunction identify data elements that are missing following the search of assessment definitions 22 and patient data database 20 based on pulmonology specific evidence based guidelines and best practices. Units 30 and 22 also initiate a search for the missing data elements from various accessible data sources (within system 10 and external to system 10) for the missing data elements based on the pulmonology specific evidence based guidelines and best practices. Units 30 and 22 compile the acquired multiple system observations related to a pulmonology specialty and expected results into a view for display. A user in step 3 accesses the display of the pulmonology related observations thereby obviating any need for burdensome manual searching of pulmonology related patient data. This facilitates patient diagnosis and treatment.

FIG. 7 illustrates organizing clinically significant data for an oncology specialist in response to determination of an abnormal HCT for a patient having medical data accessible by system 10 and in response to endocrinology observations having been defined by units 22, 30 and 32. Column 703 and corresponding columns 705 and 710 indicate user functional interaction steps and rules applied by units 22, 30 and 32 in organizing patient clinical data for an oncology specialist.

In response to detection of a patient abnormal HCT value, a user selects a type of information to be displayed based on cancer as a working diagnosis in step 1. In step 2 units 30 and 32 in conjunction execute rules in response to identifying a secondary contextual factor as being cancer. Units 30 and 32 initiate a search of assessment definitions 22 and patient data database 20 for observations and data elements related to cancer including, observations and data concerning multiple systems. The multiple system observations include respiratory system observations (abnormal chest radiography, bronchoscopy, biopsy), cardiovascular system observations (DVT, abnormal coagulation), integument system observations (moles, lumps, sun exposure), medical history (weight loss, family members with cancer, previous biopsies, fractures, radiation exposure) and laboratory test results (bone marrow, coagulation, CEA, calcium, peripheral smear). Units 30 and 32 in conjunction identify and search for data elements that are missing following the search of assessment definitions 22 and patient data database 20 based on cancer specific evidence based guidelines and best practices using various accessible data sources (within system 10 and external to system 10). Units 30 and 22 compile the acquired multiple system observations related to a cancer specialty and expected results into a view for display. A user in step 2 accesses the display of the cancer related observations and searches for signs and risks of cancer to facilitate patient diagnosis and treatment.

FIG. 8 illustrates organizing clinically significant data for an endocrinology specialist in response to determination of an abnormal HCT for a patient having medical data accessible by system 10. Column 803 and corresponding columns 805 and 810 indicate user functional interaction steps and rules applied by units 22, 30 and 32 in organizing patient clinical data for an endocrinology specialist.

In response to detection of a patient abnormal HCT value in step 1 (column 803) and user selection of an endocrinology specialty view in step 2, units 30 and 32 in conjunction initiate a search of assessment definitions 22 and patient data database 20 for observations and data elements related to an endocrinology specialty including, observations and data concerning multiple systems. The multiple system observations include respiratory system observations (chest radiology, pulmonary function tests, oxygen saturation results, arterial blood gas results), cardiovascular system observations (blood pressure, heart rate, ECG, echocardiogram, MUGA, cardiac catheterization, capillary refill), integument system observations (skin color and characteristics, cyanosis, clubbing, edema) and medical history (bronchitis, pneumonia, smoking, alpha-1 antitrypsin deficiency, asbestos exposure, occupational history, chemical exposure, laboratory test results, CBC, CMP, serum iron, HIV). Units 30 and 32 in conjunction identify data elements that are missing following the search of assessment definitions 22 and patient data database 20 based on endocrinology specific evidence based guidelines and best practices. Units 30 and 32 in conjunction identify and search for data elements that are missing following the search of assessment definitions 22 and patient data database 20 based on endocrinology specific evidence based guidelines and best practices using various accessible data sources (within system 10 and external to system 10). Units 30 and 22 compile the acquired multiple system observations related to an endocrinology specialty and expected results into a view for display. A user in step 3 accesses the display of the endocrinology related observations and searches for signs and risks of endocrinological ailments to facilitate patient diagnosis and treatment.

FIG. 9 illustrates organizing clinically significant data for a further oncology specialty in response to determination of an abnormal HCT for a patient having medical data accessible by system 10 and in response to endocrinology observations as well as observations relating to a working diagnosis of cancer, previously being defined by units 22, 30 and 32. Column 903 and corresponding columns 905 and 910 indicate user functional interaction steps and rules applied by units 22, 30 and 32 in organizing patient clinical data for an oncology specialist.

In response to detection of a patient abnormal HCT value, a user selects a type of inform-nation to be displayed based on expected results and observations in step 1. In step 2, units 30 and 32 in conjunction, execute rules in response to identifying a tertiary contextual factor comprising expected results and observations. Units 30 and 32 initiate a search of assessment definitions 22 and patient data database 20 for observations and data elements related to cancer, including observations and data concerning multiple systems. The multiple system observations include respiratory system observations (presence of a tumor on a radiography image, presence of malignant cells on bronchoscopy or biopsy), cardiovascular system observations (DVT, abnormal coagulation), integument system observations (moles, lumps, sun exposure, warts), medical history (weight loss, family members with cancer, previous biopsies, fractures, radiation exposure) and laboratory test results (bone marrow, coagulation, CEA, PSA, BRCA-1, calcium, peripheral smear). Units 30 and 32 in conjunction identify and search for data elements that are missing following the search of assessment definitions 22 and patient data database 20 based on cancer specific evidence based guidelines and best practices using various accessible data sources (within system 10 and external to system 10). Units 30 and 22 compile the acquired multiple system observations related to a cancer specialty and expected results into a view for display. A user in step 2 accesses the display of the cancer related observations and searches for signs and risks of cancer to facilitate patient diagnosis and treatment.

Data in assessment list display 36 (FIG. 1) and data provided by rules evaluation unit 32 is stored in Patient Information Database 20 through interfaces 24 and 21 respectively. Database 20 also stores data acquired from external systems 50 through interface 51. External systems 50 provide data for storage in database 50 using a variety of known communication systems such as an interface engine, for example.

Figure 10:
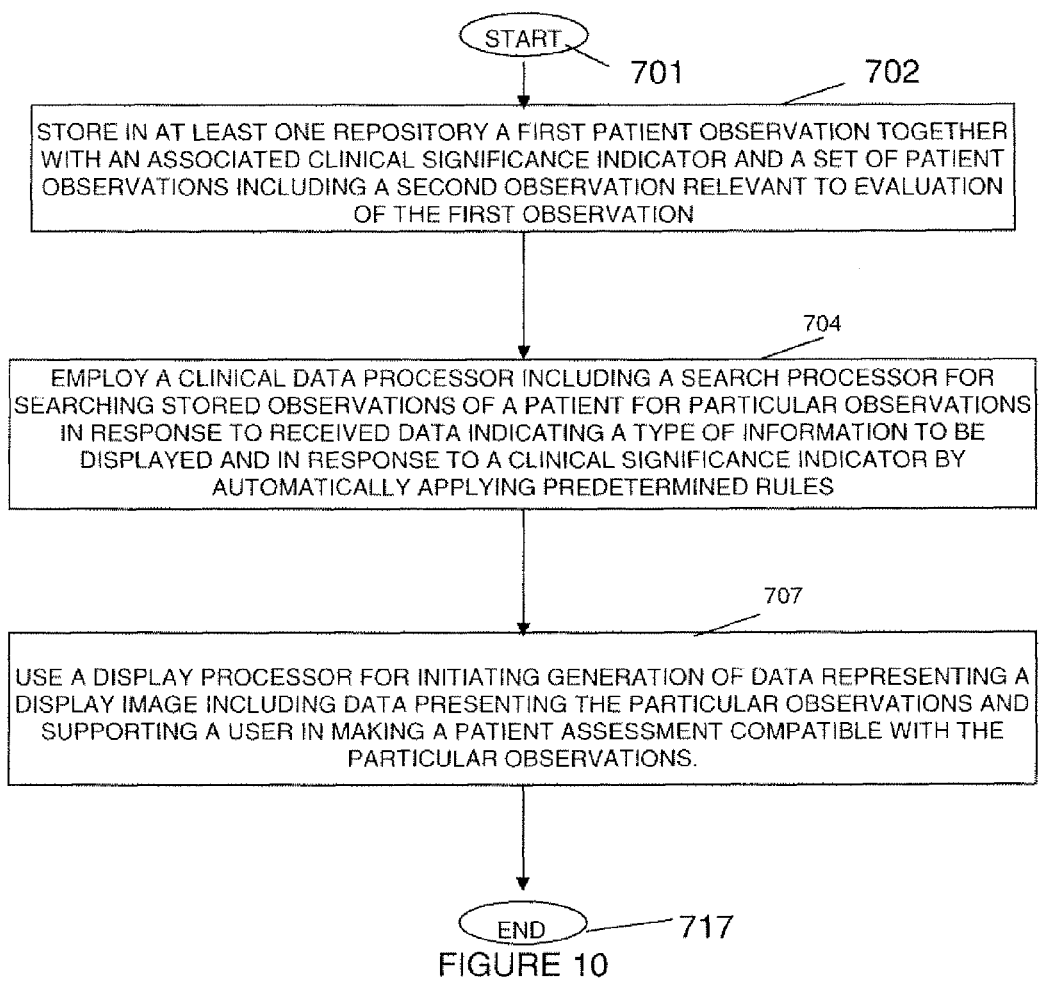
FIG. 10 shows a flowchart of a process used by a clinical data processing system, according to invention principles.

FIG. 10 shows a flowchart of a process used by CSDS 30 in conjunction with units 20, 22 and 32. In step 702 following the start at step 701 repository 20 stores a first observation together with an associated clinical significance indicator and a set of patient observations including a second observation relevant to evaluation of the first observation. The associated relevant set of patient observations are derived from one or more of, patient medical history, family medical history, a patient diagnosis, a patient complaint, a patient allergy record, a patient medication and a patient problem list. The associated relevant set of patient observations are derived also from one or more of, a treating physician specialty, medical insurance information and other patient medical parameter values.

A clinical data processor in CSDS 30 includes a search processor that in step 704 searches observations of a patient stored in repository 20 for particular observations in response to received data indicating a type of information to be displayed and in response to a clinical significance indicator of a first observation of the patient. This is done by automatically applying predetermined rules (an individual rule or sets of rules) adaptively selected and conditioned in response to whether the clinical significance indicator of the first observation indicates an abnormal, normal or critical observation. In one embodiment, the clinical data processor selects a set of rules to apply from multiple different sets of rules associated with corresponding multiple different clinical significance indicators (e.g., different sets of rules are associated with at least two of, abnormal, normal and critical clinical significance indicators), in response to a clinical significance indicator.

The search processor applies the adaptively selected predetermined rules to select the particular observations from the stored observations of the patient. The predetermined rules initiate selection, addition or exclusion of an observation from the particular observations by the clinical data processor. The type of information to be displayed comprises user entered data indicating at least one of, a patient diagnosis, a medical specialty and an expected observation. The patient diagnosis comprises cancer and the medical specialty comprises pulmonology, oncology, endocrinology or cardiology, for example. A clinical significance indicator associated with all observation comprises an indicator indicating an observation is abnormal, normal or critical (indicating a substantial impairment of patient medical condition).

The clinical data processor automatically provides data for display in multiple different images including an image enabling a user to select an individual image of the multiple different images to be displayed. A display processor in system 10 in step 707 initiates generation of data representing a display image including data presenting the particular observations (a set of observations, including first and second observations, for example) and supporting a user in making a patient assessment compatible with the particular observations. The process of FIG. 10 terminates at step 717.

The systems and processes presented in FIGS. 1 through 10 are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system according to invention principles is applicable to organize and analyze information using indicators identifying the nature of the information to automate adaptive display of a view of the information in various contexts (not just healthcare). Further, any of the functions provided in the system of FIG. 1 may be implemented in hardware, software or a combination of both and may reside on one or more processing devices located at any location of a network linking the FIG. 1 elements or another linked network including another intra-net or the Internet.

What is claimed is:

1. A computer implemented system for use in processing patient clinical data for access by a user, comprising:
   a repository associating an observation with a clinical significance indicator and with data comprising observations including laboratory test results and measured patient medical parameter values contextually relevant to evaluation of said observation having said associated clinical significance indicator;
   a clinical data processor operating using stored machine readable instructions and being electrically coupled to said repository, for using said repository for automatically adaptively providing data for display in response to receiving data representing an input observation tagged with a clinical significance indicator, said data for display comprising a first set of clinical information pertinent to the input observation if the received clinical significance indicator identifies the input observation as normal and a different second set of clinical information, including additional clinical observations absent from said first set, pertinent to the input observation if the received clinical significance indicator identifies the input observation as abnormal, the first and second set of clinical information supporting a user in making a patient assessment by including said input observation and associated contextually relevant clinical data items including the clinical significance indicator and data comprising laboratory test results and measured patient medical parameter values of the patient contextually relevant to evaluation of said observation having said associated clinical significance indicator derived from said repository; and
   a display processor operating using stored machine readable instructions and being electrically coupled to said repository, for initiating generation of data representing an image including said data for display.

2. A system according to claim 1, wherein
   said clinical data processor adaptively adds or excludes clinical observations from said second set in response to said received clinical significance indicator,
   an observation comprises a value of a patient medical parameter and
   a clinical significance indicator associated with an observation comprises an indicator indicating an observation is critical indicating a substantial impairment of patient medical condition and said data for display comprises a third set of clinical information pertinent to the input observation in response to the received clinical significance indicator identifying the input observation as critical and including
   a search processor operating using stored machine readable instructions, for searching stored observations of a patient for particular observations in response to received data indicating a type of information to be displayed comprising user entered data indicating at least one of, (a) a patient diagnosis, (b) a medical specialty and (c) an expected observation and providing a clinical significance indicator of a first observation of said patient comprising at least one of, (i) an abnormal indication and (ii) a critical indication.

3. A system according to claim 2, wherein
said search processor automatically applying predetermined rules adaptively selected in response to said clinical significance indicator of said first observation to select said particular observations from said stored observations of said patient and
said patient medical parameter comprises at least one of, (a) a blood pressure parameter, (b) a ventilation parameter, (c) a vital sign parameter, (d) a blood oxygen concentration representative parameter, (e) a spontaneous tidal volume parameter, (f) a respiratory rate parameter, (g) a positive end-expiratory pressure parameter, (h) a temperature, (i) a heart rate, (j) a cardiac output, (k) an infusion pump parameter associated with fluid delivery, (l) a drip medication related parameter and (m) another fluid related parameter.

4. A system according to claim 2, wherein
said patient medical parameter comprises at least one of, (a) a laboratory test result and (b) a parameter acquired from a medical history record of said patient.

5. A system according to claim 1, wherein
said first set of clinical information comprises a first diagnosis and said different second set of clinical information comprises a different second diagnosis previously stored by a user and
said clinical data processor automatically provides data for display in a plurality of different images including an image enabling a user to select an individual image of said plurality of different images to be displayed.

6. A system according to claim 1, wherein
said clinical data processor adaptively adds or excludes clinical observations from said second set in response to a determined user medical specialty and
said associated relevant observations are derived from at least one of, (a) patient medical history, (b) family medical history, (c) a patient diagnosis, (d) a patient complaint, (e) a patient allergy record, (f) a patient medication and (g) a patient problem list.

7. A system according to claim 1, wherein
said associated relevant observations are derived from at least one of, (a) a treating physician specialty, (b) medical insurance information and (c) other patient medical parameter values.

8. A computer implemented system for use in processing patient clinical data for access by a user, comprising:
at least one repository including a first observation together with an associated clinical significance indicator and a second observation comprising a laboratory test result or a measured patient medical parameter value of the patient contextually relevant to evaluation of said first observation;
a clinical data processor operating using stored machine readable instructions and being electrically coupled to said at least one repository, for using said at least one repository and for automatically applying predetermined rules adaptively conditioned based on said clinical significance indicator of said first observation, said predetermined rules determining whether said second observation is contextually relevant to evaluation of said first observation having said associated clinical significance indicator and is to be provided in information supporting a user in making a patient assessment compatible with said first and second observations and for automatically adaptively providing data for display in response to receiving data representing the first observation tagged with a clinical significance indicator, said data for display comprising a first set of clinical information pertinent to the input observation if the received clinical significance indicator identifies the first observation as normal and a different second set of clinical information, including additional clinical observations absent from said first set and including the second observation pertinent to the first observation if the received clinical significance indicator identifies the input observation as abnormal;
a search processor operating using stored machine readable instructions, for searching stored observations of a patient in said at least one repository to identify said second observation in response to the clinical significance indicator associated with said first observation and received data indicating a type of information to be displayed comprising user entered data indicating at least one of, (a) a patient diagnosis, (b) a medical specialty and (c) an expected observation; and
a display processor operating using stored machine readable instructions, for initiating generation of data representing an image including said information for display.

9. A system according to claim 8, wherein
said clinical data processor adaptively adds or excludes clinical observations from said second set in response to said received clinical significance indicator,
an observation comprises a value of a patient medical parameter and
a clinical significance indicator associated with an observation comprises an indicator indicating an observation is critical indicating a substantial impairment of patient medical condition and said data for display comprises a third set of clinical information pertinent to the input observation in response to the received clinical significance indicator identifying the input observation as critical and
said search processor provides said clinical significance indicator associated with said first observation and comprising at least one of, (i) an abnormal indication and (ii) a critical indication.

10. A system according to claim 8, wherein
an observation comprises a value of a patient medical parameter and
said first set of clinical information comprises a first diagnosis and said different second set of clinical information comprises a different second diagnosis previously stored by a user.

11. A system according to claim 8, wherein
said predetermined rules initiate addition or exclusion of said second observation from said information by said clinical data processor.

12. A system according to claim 8, wherein
said predetermined rules initiate selection of said second observation from a plurality of observations for inclusion in said information by said clinical data processor.

13. A system according to claim 8, wherein
said information includes a set of observations, including said first and second observations, supporting a user in making a patient assessment compatible with said set of observations.

14. A system according to claim 8, wherein
said clinical data processor adaptively conditions said predetermined rules by selecting a rule to apply from a plurality of different rules in response to whether said clinical significance indicator indicates an abnormal or non-abnormal observation.

15. A system according to claim 8, wherein
said clinical data processor adaptively conditions said predetermined rules by selecting a set of rules to apply from a plurality of different sets of rules associated with a corresponding plurality of different clinical significance indicators, in response to said clinical significance indicator of said first observation.

16. A system according to claim 15, wherein
said plurality of different sets of rules are associated with at least two of, (a) abnormal, (b) normal and (c) critical clinical significance indicators.

17. A computer implemented system for use in processing patient clinical data for access by a user, comprising:
a repository associating an observation with a clinical significance indicator and with data comprising observations including laboratory test results and measured patient medical parameter values contextually relevant to evaluation of said observation having said associated clinical significance indicator;
a search processor operating using stored machine readable instructions, for searching stored observations of a patient including said observation in said repository for particular observations in response to received data indicating a type of information to be displayed and in response to a clinical significance indicator of a first observation of said patient indicating said first observation is at least one of (a) abnormal and (b) critical; and
a display processor operating using stored machine readable instructions, for initiating generation of data representing an image for display, said image comprising a first set of clinical information pertinent to the input observation if the received clinical significance indicator identifies the input observation as normal and a different second set of clinical information, including additional clinical observations absent from said first set, pertinent to the input observation if the received clinical significance indicator identifies the input observation as abnormal, the first and second set of clinical information and including data presenting said particular observations and supporting a user in making a patient assessment compatible with said particular observations by presenting contextually relevant clinical data items including a clinical significance indicator and data comprising laboratory test results and measured patient medical parameter values of the patient contextually relevant to evaluation of said observation having said associated clinical significance indicator.

18. A system according to claim 17, wherein
said display processor adaptively adds or excludes clinical observations from said second set in response to said received clinical significance indicator and
said search processor automatically applies predetermined rules adaptively selected in response to said clinical significance indicator of said first observation to select said particular observations from said stored observations of said patient.

19. A system according to claim 17, wherein
said search processor automatically applies predetermined rules adaptively selected in response to whether said clinical significance indicator of said first observation indicates an abnormal or normal observation to select said particular observations from said stored observations of said patient.

20. A system according to claim 17, wherein
said data indicating said type of information to be displayed comprises user entered data indicating at least one of, (a) a patient diagnosis, (b) a medical specialty and (c) an expected observation.

21. A system according to claim 20, wherein
said patient diagnosis comprises cancer and
said medical specialty comprises at least one of, (a) pulmonology, (b) oncology, (c) endocrinology and (d) cardiology.

22. A system according to claim 17, wherein
said search processor searches stored observations related to, particular anatomical systems, laboratory test results and medical history, of said patient.

23. A computer implemented system for use in processing patient clinical data for access by a user, comprising:
at least one repository associating an observation with a clinical significance indicator and with data comprising observations including laboratory test results and measured patient medical parameter values contextually relevant to evaluation of said observation having said associated clinical significance indicator;
a search processor operating using stored machine readable instructions, for searching stored observations of a patient including said observation in said at least one repository for particular observations in response to received data indicating a type of information to be displayed comprising user entered data indicating at least one of, (a) a patient diagnosis, (b) a medical specialty and (c) an expected observation and in response to a clinical significance indicator of a first observation of said patient indicating said first observation is at least one of, (i) abnormal and (ii) critical, said search processor automatically applying predetermined rules adaptively selected in response to said clinical significance indicator of said first observation to select said particular observations from said stored observations of said patient; and
a display processor operating using stored machine readable instructions, for initiating generation of data representing an image for display, said image comprising a first set of clinical information pertinent to the input observation if the received clinical significance indicator identifies the input observation as normal and a different second set of clinical information, including additional clinical observations absent from said first set, pertinent to the input observation if the received clinical significance indicator identifies the input observation as abnormal, the first and second set of clinical information and including data presenting said particular observations and supporting a user in making a patient assessment compatible with said particular observations by presenting contextually relevant clinical data items including a clinical significance indicator and data comprising laboratory test results and measured patient medical parameter values of the patient contextually relevant to evaluation of said observation having said associated clinical significance indicator.

* * * * *